United States Patent [19]

Dyer et al.

[11] Patent Number: 5,786,484

[45] Date of Patent: Jul. 28, 1998

[54] RACEMIZATION AND ASYMMETRIC TRANSFORMATION PROCESSES USED IN THE MANUFACTURE OF LEVOBUPIVACAINE AND ANALOGUES THEREOF

[75] Inventors: Ulrich Conrad Dyer; Christopher James Lock; Martin Woods, all of Cambridge, United Kingdom

[73] Assignee: Chiroscience Limited, United Kingdom

[21] Appl. No.: 809,941

[22] PCT Filed: Sep. 22, 1995

[86] PCT No.: PCT/GB95/02247

§ 371 Date: May 30, 1997

§ 102(e) Date: May 30, 1997

[87] PCT Pub. No.: WO96/09290

PCT Pub. Date: Mar. 28, 1996

[30] Foreign Application Priority Data

Sep. 23, 1994 [EP] European Pat. Off. ............. 94306962
Mar. 10, 1995 [GB] United Kingdom .................. 9504927

[51] Int. Cl.$^6$ ..................... C07D 211/30; A61K 31/445
[52] U.S. Cl. ............................................ 546/225; 514/330
[58] Field of Search ........................... 546/225, 245; 514/330

[56] References Cited

PUBLICATIONS

Fyhr, P. and Hogstrom, C.: A Preformulation Study on the Kinetics of the racemization of Ropivacaine hydrochloride Acta Pharm. Suecica vol. 25(3), pp. 121–132, 1988.

Shiraiwa, T. et al.: Asymmetric Transformations of Proline and 2–Piperidinecarboxylic Acid via Formation of Salts with Optically Active Tartaric Acid Bull. Chem. Soc. Jpn., vol. 64, pp. 3251–3255, 1991.

*Primary Examiner*—Alan L. Rotman
*Assistant Examiner*—Charanjit S. Aulakh
*Attorney, Agent, or Firm*—Saliwanchik, Lloyd & Saliwanchik

[57] ABSTRACT

A process for the racemisation of an optically-enriched piperidine-2-carboxanilide compound, comprises heating the compound in the presence of an alkanoic or arylalkanoic acid. A process for the asymmetric transformation of such a compound comprises heating the compound in the presence of an acid as defined above, a chiral acid resolving agent and an inert cosolvent.

18 Claims, No Drawings

RACEMIZATION AND ASYMMETRIC TRANSFORMATION PROCESSES USED IN THE MANUFACTURE OF LEVOBUPIVACAINE AND ANALOGUES THEREOF

This application is a 371 of PCT/GB95/02247 which is now published as WO96/09290.

1. Field of the Invention

This invention relates to the racemisation and dynamic resolution of optically-enriched heterocyclic carboxanilides, e.g. piperidine-2-carboxanilides such as levobupivacaine.

2. Background of the Invention

Compounds of formula 1 (see formulae, below) wherein $R^1$ is methyl, n-propyl, n-butyl or cyclopropyl and $R^2$ is a 2,6-dimethylphenyl have utility as local anaesthetics. Biological studies have shown that (S)-enantiomers of such compounds display lower cardiotoxicity than the corresponding racemates whilst maintaining the same anaesthetic potency, and are therefore potentially more beneficial for clinical uses. Thus there is a requirement for efficient processes to manufacture compounds of formula 1 in the form of single enantiomers. For this purpose, conventional resolution approaches invariably afford up to 50% of the unwanted enantiomer. To improve atom utilisation in such processes, it is desirable to recycle the unwanted enantiomer by effecting its racemisation to provide material suitable for subsequent resolution. Additional benefits may be attainable by "asymmetric transformation", comprising simultaneous racemisation and crystallisation-induced resolution in a one-pot process.

Fyhr et al, Acta Pharm. Suecica 25(3):121–132 (1988), disclose the racemisation of ropicavaine hydrochloride (1.HCl, $R^1$=n-propyl, $R^2$=2,6-dimethylphenyl, absolute configuration =S) in dilute aqueous solution at pH 1–6, using HCl, and 80°–130° C. The results are presented as a pre-formulation stability study and merely serve to indicate that ropivacaine racemises slowly in aqueous media.

Shiraiwa et al, Bull. Chem. Soc. Jpn. 64:3251–3255 (1991), disclose asymmetric transformation of 2-piperidine-carboxylic acid, by heating in an alkanoic acid solvent in the presence of an chiral acid resolving agent and an aldehyde. The latter component is believed to assist racemisation by formation of a cationic Schiff base intermediate, a mechanistic pathway which can also operate on piperidine-2-carboxanilides 1 only in cases where $R^1$=H. Again, this process is unsuitable for operation on a manufacturing scale, not least because it uses environmentally-unacceptable reagents.

SUMMARY OF THE INVENTION

The present invention is based on the surprising discovery that N-heterocyclic-2-carboxanilides, including compounds of formula 1 wherein $R^1$ is H, methyl, n-propyl, n-butyl or cyclopropyl and $R^2$ is phenyl optionally substituted with one or more methyl groups, undergo rapid racemisation when heated in solution in the presence of a carboxylic acid $R^3CO_2H$ wherein $R^3$ is either n-alkyl or aryl (exemplified in Scheme 1) or any acid having a pKa of −1 to +6, relative to water. The reaction can be carried out in a wholly or substantially non-aqueous system, e.g. either in a solution of neat acid or in the presence of an inert cosolvent such as xylene or toluene. The presence of residual salt forms of compounds of formula 1, e.g. as the result of resolution using a chiral resolving agent, do not impede the efficiency of the process.

A preferred embodiment of the invention is the racemisation of bupivacaine (1, $R^1$=n-butyl, $R^2$=2,6-dimethylphenyl) enriched in one enantiomer, preferably the (R)-enantiomer, by heating with propanoic acid or butanoic acid. A suitable cosolvent such as xylene allows the reaction to be conducted at optimum temperature, i.e. about 130° C. Compared to the prior art, this process, and processes of the invention in general, afford significant advantages since neither dilute aqueous solutions ([1]<50 mM) nor extended reactions times are required.

As a further feature of the invention, it has been discovered that asymmetric transformation of the N-heterocyclic-2-carboxanilides can be achieved by including a chiral acid resolving agent as an additional component in the processes described above (exemplified in Scheme 2).

Two variants of such transformations are possible: firstly, a one-pot process in which a given enantiomer of the carboxanilide is converted to its optical antipode by heating to effect racemisation, followed by addition of a chiral acid, resulting in diastereoselective crystallisation of a salt; and secondly, the use of pre-formed racemic carboxanilide as a starting material. Any suitable chiral acid can be used; examples include L- and D-tartaric acid, and O,O-dibenzoyl and O,O-ditoluoyl derivatives thereof; (R)- and (S)-10-camphorsulphonic acid;

(R)- and (S)-mandelic acid; (R)- and (S)-malic acid; (R)- and (S)-1,1'-binaphthyl-2,2'-diyl hydrogen phosphate; and abietic acid.

An important aspect of this invention relates to the ability to operate the process on an industrial scale.

This in turn means that the optically-enriched carboxanilides themselves, e.g. obtained by resolution but to an extent that the predominant enantiomer is insufficiently enantiopure for immediate use, become useful products. This applies to mixtures of enantiomers in which one, usually the (R)-enantiomer, is present in an enantiomeric excess of 20 to 80%, preferably 25 to 75%, more preferably 30 to 70%, and most preferably 35 to 65%, with respect to its optical antipode. For example, a mixture enriched in (R)-bupivacaine can be used practically, by racemisation of the mixture and subsequent resolution.

The following Example illustrates the invention.

EXAMPLE

A stirred mixture of (S)-bupivacaine (0.140 g, 0.49 mmol) and propanoic acid (3.5 ml) was heated to reflux under a nitrogen atmosphere for 7 hours. The resulting solution was cooled and then poured into a mixture of distilled water (20 ml) and ethyl acetate (20 ml). Aqueous ammonia (28% w/v) was added until the pH of the aqueous layer was 10. The organic layer was separated and the aqueous layer extracted with ethyl acetate (20 ml). The combined organic extracts were washed with distilled water (20 ml), dried ($MgSO_4$) and concentrated under reduced pressure to give racemic bupivacaine (0.137 g, 98%).

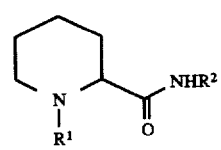

(1)

Scheme 1

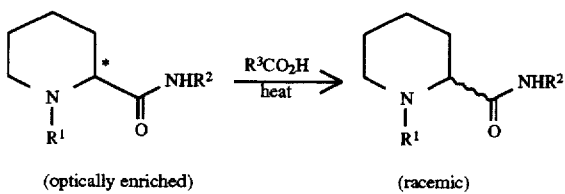

(optically enriched) → (racemic)

Scheme 2

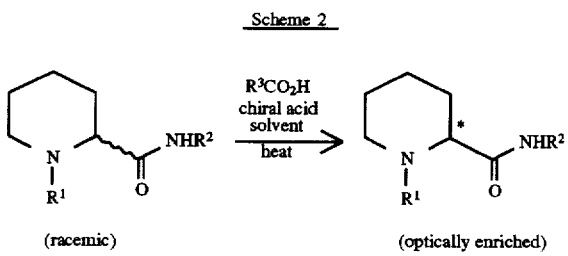

(racemic) → (optically enriched)

We claim:

1. A process for the racemisation of an optically-enriched N-containing heterocyclic compound having 3 to 7 ring atoms and a carboxanilide group attached to the ring at a carbon atom in the 2-position adjacent to the N-atom, said carbon atom being the chiral center to be racemised, wherein said N-atom is substituted with an $R_1$ substituent and said $R_1$ substituent is not H, said method comprising heating the compound in a wholly or substantially non-aqueous system comprising an acid selected from the group consisting of alkanoic acids, arylalkanoic acids and acids having a pKa of −1 to +6, relative to water.

2. The process according to claim 1, wherein the compound is a piperidine-2-carboxanilide.

3. The process according to claim 1, wherein the compound is of formula (1)

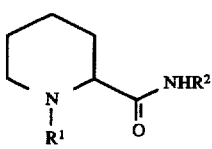 (1)

wherein $R^1$ is a substituent of up to 20 C atoms and $R^2$ is alkyl or aryl of up to 20 C atoms.

4. The process according to claim 3, wherein $R^2$ is $C_{6-20}$ aryl.

5. The process according to claim 4, wherein $R^1$ is $C_{1-6}$ alkyl and $R^2$ is phenyl optionally substituted with one or more $C_{1-4}$ alkyl groups.

6. The process according to claim 5, wherein the starting material is optically-enriched bupivacaine, wherein $R^1$ is n-butyl and $R^2$ is 2,6-dimethylphenyl.

7. The process according to claim 6, wherein the starting material is enriched in the (R)-enantiomer.

8. The process according to claim 5, wherein $R^1$ is selected from the group consisting of methyl, n-propyl and cyclopropyl and $R^2$ is 2,6-dimethylphenyl.

9. The process according to claim 1, wherein the racemisation is carried out in a solution of the acid, neat or mixed with an inert cosolvent.

10. The process according to claim 9, wherein a solution of optically-enriched bupivacaine is heated in propanoic acid or butanoic acid.

11. A process for the asymmetric transformation of a compound as defined in claim 1, which comprises heating the compound in the presence of an acid selected from the group consisting of alkanoic acids, arylalkanoic acids and acids having a pKa of −1 to +6, relative to water, a chiral acid resolving agent, and an inert cosolvent.

12. The process according to claim 11, wherein the compound, optically-enriched in a given enantiomer, is converted to its optical antipode.

13. The process according to claim 11, wherein said racemic compound is transformed.

14. The process according to claim 1, wherein the acid is an alkanoic or arylalkanoic acid.

15. The process according to any of claim 1, wherein the acid has the given pKa.

16. The mixture of enantiomers of a compound as defined in claim 1, the mixture comprising the (R)-enantiomer in an excess of 20 to 80%, with respect to the (S)-enantiomer.

17. The mixture according to claim 16, wherein the excess is 30 to 70%.

18. A process for the manufacture of levobupivacaine, which comprises racemisation of the mixture of enantiomers of a compound of claim 1, said mixture comprising the (R)-enantiomer in excess of 20 to 80 % with respect to the (S)-enantiomer, and subsequent resolution.

* * * * *

UNITED STATES PATENT AND TRADEMARK OFFICE
CERTIFICATE OF CORRECTION

PATENT NO. : 5,786,484

DATED : July 28, 1998

INVENTOR(S) : Ulrich C. Dyer, Christopher J. Lock and Martin Woods

It is certified that error appears in the above-identified patent and that said Letters Patent is hereby corrected as shown below:

Column 3, line 40: Delete " 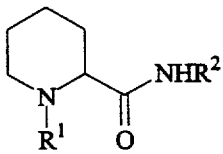 (1)"

and insert

--(1) 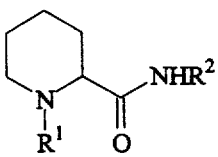 --.

UNITED STATES PATENT AND TRADEMARK OFFICE
CERTIFICATE OF CORRECTION

PATENT NO. : 5,786,484

DATED : July 28, 1998

INVENTOR(S) : Ulrich C. Dyer, Christopher J. Lock and Martin Woods

It is certified that error appears in the above-identified patent and that said Letters Patent is hereby corrected as shown below:

<u>Column 4, line 34:</u> Delete "The process according to any of claim 1" and insert --the process according to claim 1--.

Signed and Sealed this

Twentieth Day of October, 1998

Attest:

BRUCE LEHMAN

Attesting Officer

Commissioner of Patents and Trademarks